United States Patent
Tokunaga et al.

(10) Patent No.: US 6,824,670 B2
(45) Date of Patent: Nov. 30, 2004

(54) SAMPLE DISCRIMINATING METHOD

(75) Inventors: Hiroyuki Tokunaga, Matsuyama (JP); Shoji Miyazaki, Matsuyama (JP); Hideyuki Baba, Matsuyama (JP); Yoichi Inoue, Osaka (JP); Kazuo Iketaki, Otsu (JP); Katsumi Hamamoto, Otsu (JP)

(73) Assignees: Matsushita Electric Industrial Co. Ltd., Osaka (JP); Arkray, Inc., Kyoto (JP)

( * ) Notice: Subject to any disclaimer, the term of this patent is extended or adjusted under 35 U.S.C. 154(b) by 295 days.

(21) Appl. No.: 09/890,097
(22) PCT Filed: Nov. 29, 2000
(86) PCT No.: PCT/JP00/08393

§ 371 (c)(1),
(2), (4) Date: Oct. 29, 2001

(87) PCT Pub. No.: WO01/40787

PCT Pub. Date: Jun. 7, 2001

(65) Prior Publication Data

US 2002/0139692 A1 Oct. 3, 2002

(30) Foreign Application Priority Data

Nov. 29, 1999 (JP) ............................................. 11-337730

(51) Int. Cl.[7] ........................ G01N 27/26; G01N 27/327
(52) U.S. Cl. ........................................ 205/792; 205/775
(58) Field of Search ............................. 205/775, 777.5, 205/787, 789, 792, 787.5, 782, 780.5, 778.5, 775.5; 204/400, 401, 403.01, 416, 431, 433; 702/19, 22, 23

(56) References Cited

U.S. PATENT DOCUMENTS 5,653,863 A  8/1997  Genshaw et al. ........ 205/777.5

FOREIGN PATENT DOCUMENTS

JP  11-230934 A  *  8/1999  ......... G01N/27/416

OTHER PUBLICATIONS

JPO machine translation of Yuichiro et al. (JP 11–230934).*

* cited by examiner

*Primary Examiner*—Alex Noguerola
(74) *Attorney, Agent, or Firm*—Birch, Stewart, Kolasch & Birch, LLP

(57) ABSTRACT

A glucose sensor system comprising the steps of using as a sample discriminating parameter a ratio ($I/\Delta I$) of a measured current value I to the time-differential value of the current value $\Delta I$, defining a discrimination function that discriminates whether a sample is blood or control fluid and uses the discriminating parameter as an independent variable, quantitating as a discriminating index a numeric value obtained by substituting a discriminating parameter value into this discrimination function, and automatically discriminating, based on this index, whether the sample is blood or a control fluid, whereby a kind of the sample can be automatically quantitated by measuring electric current when a sensor system is used for quantitating the concentration of an analysis object in the sample.

6 Claims, 3 Drawing Sheets

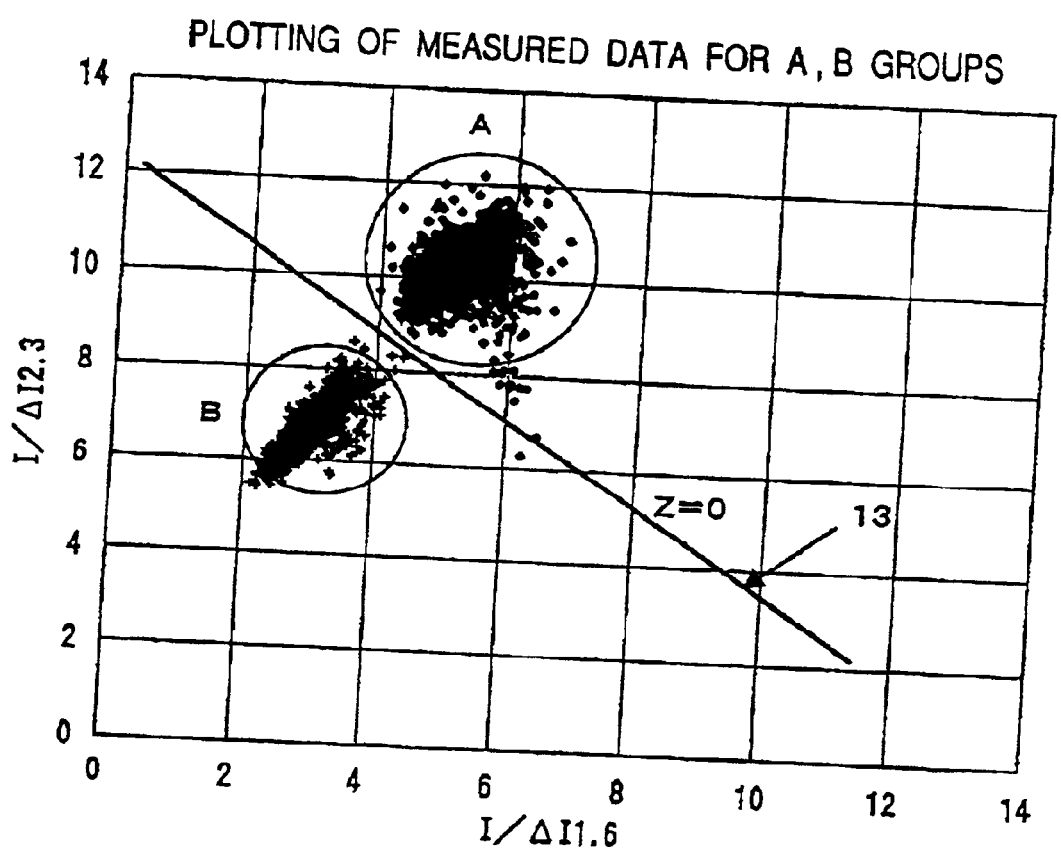

SAMPLE DISCRIMINATING METHOD

This application is the national phase under 35 U.S.C. § 371 of PCT International Application No. PCT/JP00/08393 which has an International filing date of Nov. 29, 2000, which designated the United States of America and was not published in English.

TECHNICAL FIELD

The present invention relates to a method of discriminating a sample for a sensor system which measures the concentration of a target substance (substance of interest) contained in the sample, in particular for a biosensor system which quantitates the concentration of glucose, cholesterol or the like contained in a body fluid such as blood by measuring electric current. More particularly, it relates to a sample discriminating method of automatically discriminating whether the sample introduced to a sensor system is a body fluid or a standard fluid, the sensor system being designed to periodically examine whether the accuracy of the sensor system is maintained or not, using the standard fluid, whose concentration has been known, instead of the body fluid.

BACKGROUND ART

There has been well known a sensor system which quantitates the concentration of a target substance contained in a sample by measuring electric current. In recent years, the sensor system described above has been widely applied to, for example, a biosensor system such as a small and easy type of blood sugar measuring system for quantitating the value of blood sugar contained in blood, or the like. Recently, the blood sugar measuring system, which is used for a blood sugar diagnosis or daily management of a diabetes patient, is commercially prevailed while being provided with many various functions. Recently, for example, the blood sugar measuring system is particularly of great importance in the field of a data management such as a management or processing of measured data.

In general, measurement accuracy of the biosensor system including a sensor and a measuring device is periodically managed using, for example, an exclusive standard fluid (referred to "control fluid" hereinafter), in order to maintain or manage the measuring accuracy. As the control fluid, there may been used a solution in which a known amount of glucose is dissolved in pure water, the solution being colored with a pigment in accordance with its use, or being provided with a hydrophilic polymer so as to adjust its viscosity.

In the conventional biosensor system in which its measurement accuracy is managed using the control fluid, it is required that the measured data of the control fluid is not confusedly processed as the measured data of the body fluid or the like used as an ordinary sample. Accordingly, before the control fluid is introduced into the biosensor system, the measuring mode is changed to that for the control fluid by a predetermined manual operation of the measuring device so as to distinguish its measuring data from the measuring data of the body fluid or the like.

However, in the conventional biosensor system described above, when the control fluid is introduced, it is required to change the measuring mode by the manual operation for changing the mode, for example, button operation or the like. In consequence, there is such a problem that the measured data for the control fluid may be managed while erroneously being recognized as the measured data for the body fluid or the like by erroneously performing or forgetting the operation. Meanwhile, there may be also such a problem that the operation for manually changing the mode is troublesome. In particular, for a diabetes patient or the like having trouble in the eyes or fingertips, it may be difficult to change the mode by the manual operation. Therefore, there is requested a biosensor system, which can automatically discriminate whether a sample introduced into the biosensor system is a body fluid or a control fluid.

DISCLOSURE OF INVENTION

The present invention, which has been developed to solve the conventional problems described above, has an subject to provide a means which can automatically discriminate the kind of a sample for a sensor system that quantitates the concentration of a target substance contained in the sample by measuring electric current, for example, a biosensor system such as a blood sugar measuring system.

A sample discriminating method according to the present invention which has been developed to achieve the above-mentioned object, is a method of discriminating a sample for a sensor system which quantitates the concentration of a target substance (substance of interest) contained in the sample by measuring electric current, the method comprising the steps of, (i) using a ratio of a measured current value to a time-differential or time-difference value of the current value as a discriminating parameter, (ii) defining a discrimination function for discriminating kinds of a plurality of objective samples, the discrimination function using the discriminating parameter as an independent variable, (iii) using a numeric value obtained by substituting the value of the discriminating parameter into the discrimination function as a discriminating index, and (iv) automatically discriminating the kind of any sample based on the discriminating index.

As the discriminating function, for example, there may be given a discriminant function, a Mahalanobis distance or the like.

According to the sample discriminating method of the present invention, because the kind of the sample can be automatically discriminated, the kind of the sample may not be erroneously recognized due to erroneously performing or forgetting the operation. Further, because it is not necessary to change the mode by a manual operation, even a person having trouble in the eyes or fingertips can easily use the sensor system.

The discrimination function may be defined by means of an equation using only one discriminating parameter or independent variable. However, in order to raise the accuracy of the discrimination, it is more preferable that the discrimination function is defined by means of an expression using a plurality of, for example two, discriminating parameters or independent variables.

The discrimination function may be defined by means of a linear expression for the discriminating parameter. Meanwhile, the discrimination function may be defined by means of a expression of high degree, for example an expression of nth degree (n=2, 3, 4, . . . ), for the discriminating parameter.

The sample discriminating method according to the present invention is particularly effective for such a case that the kinds of the samples to be discriminated are a body fluid such as blood and a control fluid. In this case, it is preferable that the sensor system is automatically judged whether it is right or not, namely the system is checked, based on a quantitated value of the concentration of the target substance in the control fluid, and then a resultant judgement is indicated.

Meanwhile, in the sample discriminating method according to the present invention, it is preferable that when the value of the discriminating index is within such a predetermined range that it is difficult to discriminate the kind of the sample, namely it exists within a region near a boundary, the kind of the sample is not automatically discriminated while it is indicated that the discrimination has not been performed. If so, the accuracy or preciseness of the automatic discrimination of the kind of the sample may be highly improved.

Although it may be a rare case that the kind of the sample is not automatically discriminated so that it is indicated that the discrimination has not been performed, the kind of the sample may be designated by a manual operation in the above-mentioned case.

BRIEF DESCRIPTION OF DRAWINGS

FIG. 3 is a view obtained by plotting each of the sample data according to an embodiment of the present invention, based on the discriminating parameter.

BEST MODE FOR CARRYING OUT THE INVENTION

Hereinafter, an embodiment of the present invention will be concretely described in detail with reference to the accompanied drawings.

Figure 1A:
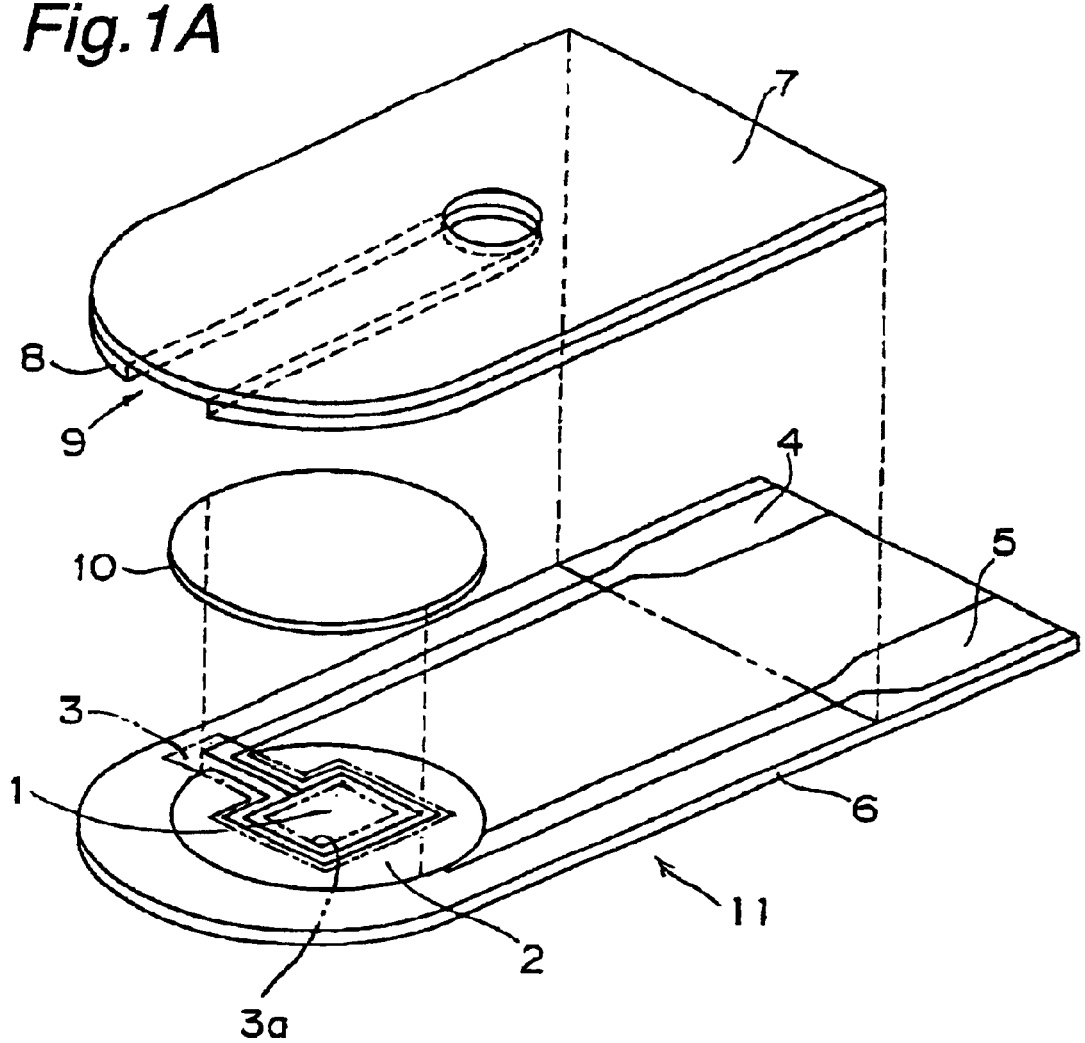
FIG. 1A is an exploded perspective view of a sensor in a glucose sensor system using a sample discriminating method according to the present invention.
Figure 1B:
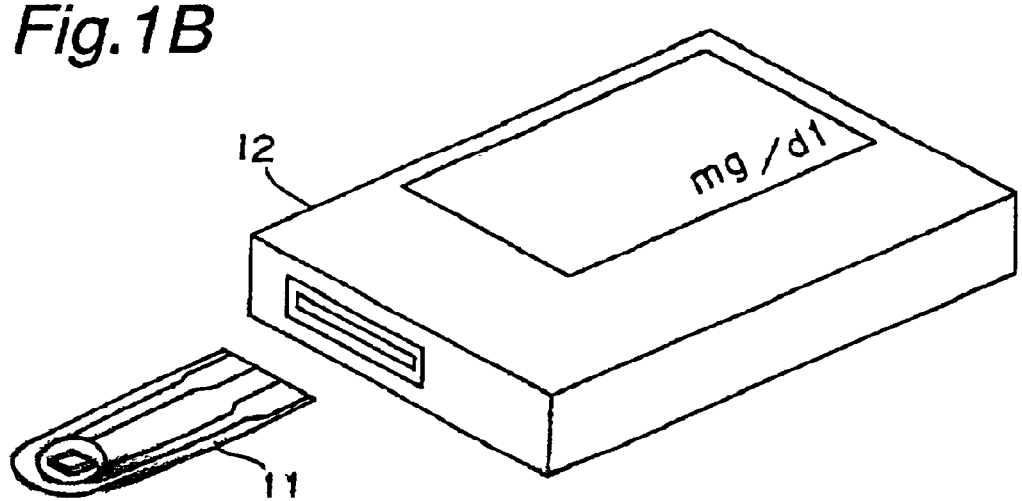
FIG. 1B is a perspective view of a biosensor system including the sensor shown in FIG. 1A and a measuring device.

FIGS. 1A and 1B show a glucose sensor system for quantitating the concentration of glucose contained in a blood sample, namely the blood sugar value, as an example of biosensor systems, the system being substantially composed of a sensor 11 and a measuring device 12.

As shown in FIG. 1A, in the sensor 11 of the glucose sensor system, on an insulating support 6 made of PET (polyethylene terephthalate), there are formed a first silver lead 4, a second silver lead 5, and an electrode section including a working electrode 1 and a counter electrode 2, each of which is made of carbon by means of screen printing. Thus, the first silver lead 4 is electrically connected to the working electrode 1 while the second silver lead 5 is electrically connected to the counter electrode 2.

Hereupon, the electric conductor composed of the first silver lead 4 and the working electrode 1 is not electrically connected, in a direct state, to the electric conductor composed of the second silver lead 5 and the counter electrode 2. However, they are electrically connected to each other through a reactive layer 10 described below.

Moreover, an insulating layer 3 is formed at an upper side of the electrode section, namely the working electrode 1 and the counter electrode 2. Hereupon, the insulating layer 3 also covers a part of the first silver lead 4. Meanwhile, within a region in which the working electrode 1 is formed if seen in the plane view, a cutoff section 3a is provided in the insulating layer 3. Therefore, a portion of the working electrode 1, which corresponds to the cutout section 3a, is exposed outward. The insulating layer 3 with the cutout section 3a is provided in order to make the exposed area of the working electrode 1 and the counter electrode 2 become constant.

The reactive layer 10 is disposed on the insulating layer 3 and the electrode section formed as described above. The reactive layer 10 includes a layer of CMC (carboxylmethyl cellulose) which is one of hydrophilic polymers, GOD (glucose oxidase) which acts as an enzyme, and potassium ferricyanide which acts as a mediator. Further, on those, there is disposed an insert 9 composed of a cover 7 and a spacer 8. Then, when a sample fluid is made contact to the insert 9, the sample of a constant amount, for example about 3 $\mu$L is introduced into the reactive layer 10 and the electrode section by means of a capillary phenomenon.

Thus, as shown in FIG. 1B, after the sensor 11 has been mounted on the measuring device 12, an electric source of the measuring device is turned on so that the device becomes such a state that it can receive a sample, namely a blood sample or a control fluid. When the sample is applied to the sensor 11, the voltage applied to the sensor 11 is shut once, and then the reaction is incubated for a predetermined time. After that, the voltage is applied again. Hereupon, the voltage is applied between the first silver lead 4 and the second silver lead 5, further between working electrode 1 and the counter electrode 2.

In consequence, electric current, which corresponds to the concentration of glucose contained in the sample, flows between the working electrode 1 and the counter electrode 2 through the reactive layer 10, while the electric current value is measured. Then, the concentration of glucose contained in the sample is quantitated on the basis of the electric current value.

In the glucose sensor system, the concentration of glucose contained in each of various kinds of blood samples is measured or quantitated. On the other hand, in order to maintain the measuring accuracy, the measuring accuracy is periodically managed using a control fluid, for example a glucose standard solution. That is, a control fluid whose glucose concentration has been known is used as a sample, while the glucose concentration is measured or quantitated. So, on the basis of an error or the like of the quantitated value, the preciseness of the resultant value measured by the glucose sensor system is examined. Hereupon, as the control fluid, there may been used a solution in which known amount of glucose is dissolved in pure water, the solution being colored with a pigment in accordance with its use, or being provided with a hydrophilic polymer so as to adjust its viscosity.

Then, in the glucose sensor system, a blood sample or a control fluid is received in the sensor 11 as a sample. In the glucose sensor system, the measuring device 12 automatically discriminates or judges whether the sample actually received in the sensor 11 is a blood sample or a control fluid. Accordingly, the kind of the sample may not erroneously recognized due to erroneously performing or forgetting the operation. Further, because it is not necessary to manually change the operation mode, even a person having trouble in the eyes or fingertips can easily use the glucose sensor system.

Hereinafter, the sample discriminating method for the measuring device 12 will be concretely described. The outline of the sample discriminating method in the measuring device 12 is as follows.

(1) There is prepared a ratio of electric current value to a time-differential or time-difference value of the electric current value as a sample discriminating parameter, the electric current value having been measured for a blood sample or a control fluid.

(2) There is defined a discrimination function for discriminating whether the sample to be measured is a blood sample or a control fluid, the discrimination function using the discriminating parameter as an independent variable.

(3) There is provided a numeric value obtained by substituting the value of the discriminating parameter into the discrimination function as a discriminating index.

(4) It is automatically discriminated whether the sample is a blood sample or a control fluid on the basis of the discriminating index.

In the present embodiment, a general expression indicated by Expression 1 described below is used as the discrimination function.

$$Z = a_1 \times \alpha + a_2 \times \beta + a_0 \qquad \text{Expression 1}$$

Z: discriminating index
α: first discriminating parameter (independent variable)
β: second discriminating parameter (independent variable)
$a_1, a_2, a_0$: constant Thus, it is judged whether the sample is a blood sample or a control fluid, for example, based on the conditions described below, using the discriminating index Z calculated in accordance with the discrimination function indicated by Expression 1. Hereupon, L and H described below mean the lower limit and upper limit of the area or range in which the above-mentioned judgement is particularly difficult, respectively.

(1) In the case of Z<L, it is judged that the sample is a control fluid.

(2) In the case of L≦Z≦H, the judgement is not performed while it is decided that the sample is un-decidable.

(3). In the case of Z>H, it is judged that the sample is a blood sample.

The discriminating parameter, which is the independent variable in the discrimination function indicated by Expression 1, namely the ratio of the measured electric current value I to its time-differential ΔI (referred to "I/ΔI" hereinafter), is defined as follows. Hereupon, "I" means the electric current value at the time point that t seconds have passed from the time point when the application of voltage has been started again (starting point of the second voltage application). However, in the case that it is particularly necessary to clearly indicate "t seconds have passed", it will be described as $I_t$.

"ΔI" means the absolute value of the difference $|I_t - I_{t+\Delta t}|$ between $I_t$ and the electric current value $(I_{t+\Delta t})$ at the time point that relatively short time Δt seconds have passed from the time point t at which $I_t$ has been measured, namely at the time point that (t+Δt) seconds have passed from the starting point of the second voltage application. Alternatively, "ΔI" may mean the absolute value of the difference $|I_t - I_{t-\Delta t}|$ between $I_t$ and the electric current value $(I_{t-\Delta t})$ at the time point that Δt seconds precede to the time point t at which $I_t$ has been measured, namely at the time point that (t−Δt) seconds have passed from the starting point of the second voltage application. Each ΔI can be similarly used as a parameter which indicates the degree or magnitude of the inclination of the wave shape of the electric current near the time point that t seconds have passed from the starting point of the second voltage application.

In the example described above, the ratio between I and ΔI is a value of I/ΔI (I÷ΔI) which is obtained when I is divided by ΔI. However, as the ratio between I and ΔI, there may be used a value of ΔI/I (ΔI÷I) which is obtained when ΔI is divided by I. In either case, the ratio can be similarly used as the discriminating parameter, even though the discrimination functions of those, which have been previously defined, are different from each other. Hereupon, the numerical value of the discriminating parameter itself reflects the property of the kind of the sample fluid. Therefore, the sample can be discriminated by merely comparing the numerical value simply to a standard value without using the discrimination function. However, in this case, there may remain such a problem that the accuracy of the discrimination of the sample is lowered a little.

I/ΔI at the time point that t seconds have passed from the starting point of the second voltage application (referred to "I/ΔI(t)" hereinafter), can be similarly used as the discriminating parameter, regardless of the value of t, namely at every time point after the measurement of electric current value has been started. However, it is preferable to use I/ΔI(t) at a current decay point in which the property of the kind of the sample fluid is well reflected relatively. The time point or frequency for calculating t and Δt may be changed in accordance with the composition of the control fluid to be discriminated.

Figure 2A:
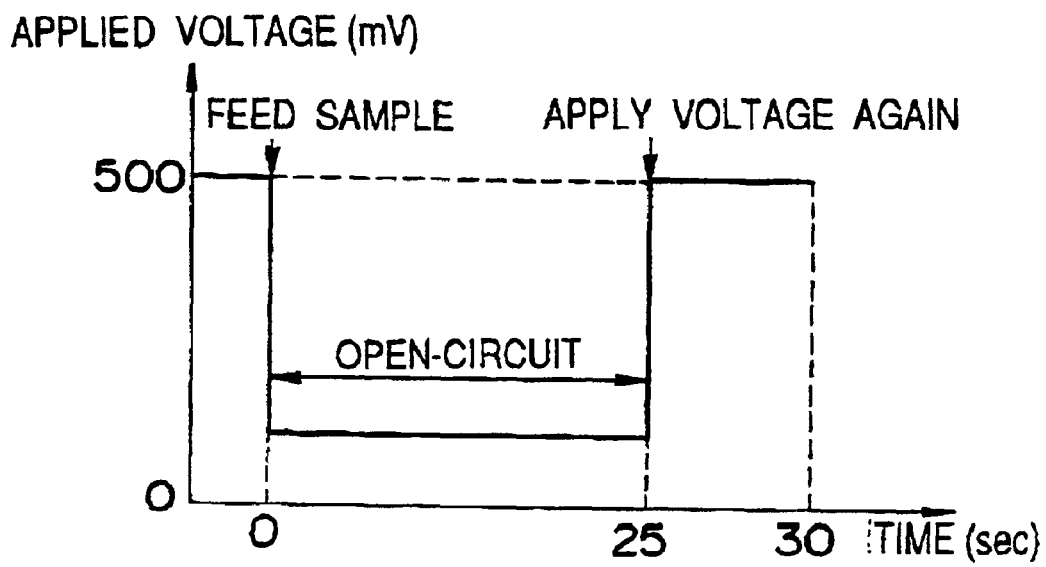
FIG. 2A is a graph showing the relation between the applied voltage or its applying pattern and the time, when the value of the electric current is measured in the glucose sensor system according to the present invention.

FIG. 2A is a graph showing the relation between the applied voltage and the time when the value of the electric current flowing actually through the sample in the reactive layer 10 is measured, that is, showing a concrete process for applying the voltage between the both silver leads 4,5 namely between the both electrodes 1,2. That is, as shown in FIG. 2A, the voltage of 500 mV is applied before the sample is supplied. Thus, after the sample has been supplied at the time point of t=0, the system is set to an open circuit state for 25 seconds so that the voltage application is shut. Then, the voltage of 500 mV is applied again for 5 seconds.

Figure 2B:
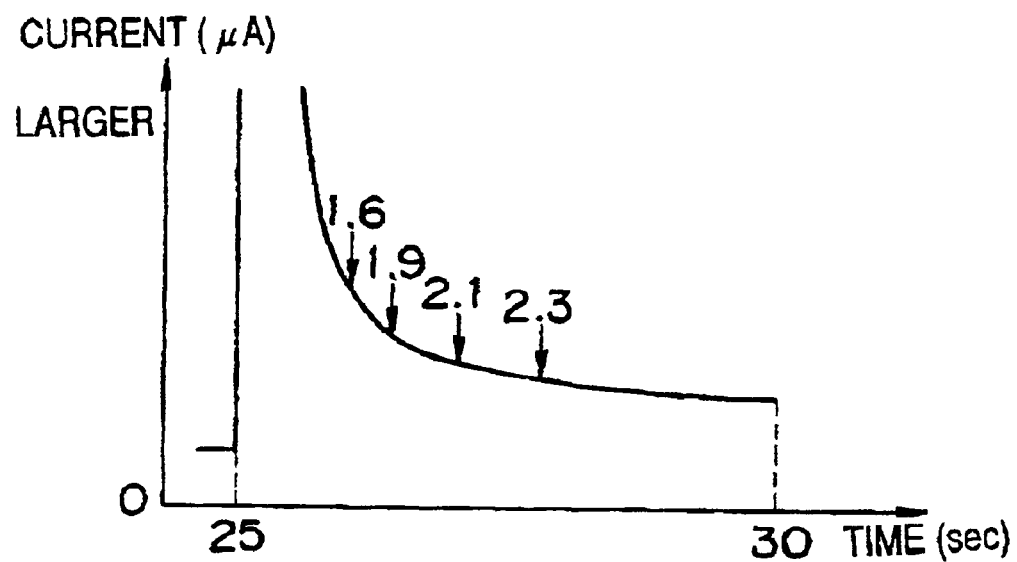
FIG. 2B is a graph showing a characteristic of the change of the electric current with lapse of time after the application of the voltage has been started again, in the case that the voltage is applied as shown in FIG. 2A.

FIG. 2B is a graph showing an example of the resultant data of the electric current (wave shape of the current) measured after the voltage has been applied again, in the case that the voltage is applied in the pattern shown in FIG. 2A. In FIG. 2B, the numerical value 1.6, 1.9, 2.1 and 2.3 indicate concrete examples of time points at which current values I used for calculating the discriminating parameter are measured, the time points indicating the elapsed times after the voltage has been applied again.

Next, there will be described a sample discriminating process in the glucose sensor system according to the present invention, namely a concrete example of a process for discriminating a blood sample and a control fluid.

In the concrete example, there were prepared a total of fifteen kinds of blood samples, whose glucose concentrations were to be measured, by setting glucose concentration to five different values while setting hematocrit values to three different values and then combining one of the glucose concentration to one of the hematocrit values. That is, the glucose concentrations were set to five kinds of 100 mg/dL, 200 mg/dL, 300 mg/dL, 400 mg/dL and 500 mg/dL. The hematocrit values were set to three kinds of 25%, 45% and 65%.

Meanwhile, as control fluids, there were prepared aqueous solutions in which PVP (polyvinyl pyrrolidone), which was a hydrophilic polymer, and glucose were dissolved in water. The glucose concentration of the aqueous solutions were set to two kinds of 85 mg/dL and 260 mg/dL. The viscosity of each of the control fluids was relatively higher.

As to each of the seventeen kinds of samples, current values were measured while applying a voltage between the both silver leads 4,5, further between the both electrodes 1,2 in the pattern or process shown in FIG. 2A. The current values were measured at every 0.1 seconds. Thus, four current values at four time points shown in FIG. 2B were selected from the current values which had been selected at every 0.1 seconds, as the current values required for defining the discrimination function. That is, these are the current value at 1.6 seconds past the starting point of the second voltage application ($I_{1.6}$), the current value at 1.9 seconds past the same ($I_{1.9}$), the current value at 2.1 seconds past the same ($I_{2.1}$) and the current value at 2.3 seconds past the same ($I_{2.3}$). These four time points or current values were obtained by means of the following procedure.

As described below, the values of $I/\Delta I$ were calculated at every 0.1 seconds using the resultant data of the current values measured as to all of the seventeen samples described above. Hereupon, the differential of the current value $\Delta I$ was $|I_t - I_{t+\Delta t}|$. The time difference $\Delta t$ was set to 0.5 seconds in order to ensure the repeatability of $I/\Delta I$. Thus, each $I/\Delta I$ was classified into two groups, namely the group A as to the measurement for the blood samples and the group B as to the measurement for the control fluids. Further, the average value for each of the groups (Aavg, Bavg) was calculated. Then, the point, in which the two average values were most apart from each other, was selected.

Sample $A_1 = I/\Delta I_{0.1}, I/\Delta I_{0.2}, I/\Delta I_{0.3}, \ldots, \ldots, \ldots, \ldots, \ldots,$
$I/\Delta I_{4.9}, I/\Delta I_{5.0}$ Sample $A_2 = I/\Delta I_{0.1}, I/\Delta I_{0.2}, I/\Delta I_{0.3}, \ldots, \ldots, \ldots, \ldots, \ldots,$
$I/\Delta I_{4.9}, I/\Delta I_{5.0}$ Sample $A_x = I/\Delta I_{0.1}, I/\Delta I_{0.2}, I/\Delta I_{0.3}, \ldots, \ldots, \ldots, \ldots, \ldots$
$I/\Delta I_{4.9}, I/\Delta I_{5.0}$ Sample $B_1 = I/\Delta I_{0.1}, I/\Delta I_{0.2}, I/\Delta I_{0.3}, \ldots, \ldots, \ldots, \ldots, \ldots$
$I/\Delta I_{4.9}, I/\Delta I_{5.0}$ Sample $B_2 = I/\Delta I_{0.1}, I/\Delta I_{0.2}, I/\Delta I_{0.3}, \ldots, \ldots, \ldots, \ldots, \ldots$
$I/\Delta I_{4.9}, I/\Delta I_{5.0}$ Sample $B_y = I/\Delta I_{0.1}, I/\Delta I_{0.2}, I/\Delta I_{0.3}, \ldots, \ldots, \ldots, \ldots, \ldots,$
$I/\Delta I_{4.9}, I/\Delta I_{5.0}$ Sample $A\text{avg} = I/\Delta I_{0.1}, I/\Delta I_{0.2}, I/\Delta I_{0.3}, \ldots, \ldots, \ldots, \ldots, \ldots,$
$I/\Delta I_{4.9}, I/\Delta I_{5.0}$ Sample $B\text{avg} = I/\Delta I_{0.1}, I/\Delta I_{0.2}, I/\Delta I_{0.3}, \ldots, \ldots, \ldots, \ldots, \ldots,$
$I/\Delta I_{4.9}, I/\Delta I_{5.0}$ In consequence, the point $I_{1.6}$ was selected, in which two groups, namely the group A as to the measurement for the blood samples and the group B as to the measurement for the control fluids, were most apart from each other. Hereupon, the current value at 1.6 seconds past the starting point of the second voltage application ($I_{1.6}$) and the current value at 2.1 seconds past the same ($I_{2.1}$) are required as the current values for defining the discrimination function $I/\Delta I_{1.6}$.

Moreover, in the case that differential of the current value $\Delta I$ was $|I_t - I_{t-\Delta t}|$, also, data processing as same as that of the above-mentioned case was performed. In this case, the time difference $\Delta t$ was set to 0.4 seconds or more in order to ensure the repeatability of $I/\Delta I$. In consequence, the point $I_{2.3}$ was selected, in which two groups, namely the group A as to the measurement for the blood samples and the group B as to the measurement for the control fluids, were most apart from each other. Hereupon, the current value at 2.3 seconds past the starting point of the second voltage application ($I_{2.3}$) and the current value at 1.9 seconds past the same ($I_{1.9}$) are required as the current values for defining the discrimination function $I/\Delta I_{2.3}$. By combining the results with the above-mentioned results, it became clear that the inclination of the current at nearly 2.0 seconds past the starting point of the second voltage application was most effective to discriminate the samples.

Even in the case that only one discriminating parameter in the above-mentioned two kinds of discriminating parameters is used, the samples can be discriminated by defining a discrimination function having one independent variable. However, it may remain such a problem that the accuracy of the discrimination is lowered a little. The reason, why $\Delta I$ is calculated in the two way as described above, is nearly as follows.

That is, in the sense of calculating the inclination of the current at nearly 2.0 seconds past the starting point of the second voltage application, the same effect may be obtained in either discriminating parameter. However, due to the property of the wave shape, there is such a tendency that the repeatability for the blood sample becomes better in the former while the repeatability for the control fluid becomes better in the latter. In consequence, the discriminating effect becomes best when two discriminating parameters are used.

Thus, the discriminating parameter used in the following calculation was calculated using the measured current values by means of the following Expression 2 and Expression 3.

$I/\Delta I_{1.6} = I_{1.6}/|I_{1.6} - I_{2.1}|$  Expression 2

$I/\Delta I_{2.3} = I_{2.3}/|I_{2.3} - I_{1.9}|$  Expression 3

Based on the whole measured results as to the seventeen kinds of samples described above, $I/\Delta I_{1.6}$ and $I/\Delta I_{2.3}$ were calculated so that the discrimination function for discriminate the samples was defined. The defined discrimination function is indicated by the following Expression 4.

$Z = 8.3014 \times |I/\Delta I_{1.6}| + 10.4381 \times |I/\Delta I_{2.3}| - 124.6603$  Expression 4

Hereinafter, a process for leading the discrimination function will be described with reference to FIG. 3.

FIG. 3 is a graph obtained by plotting a group of discriminating parameters which are calculated from the measured results as to the two groups A and B, wherein the position of the horizontal axis denotes $|I/\Delta I_{1.6}|$ while the position of the vertical axis denotes $|I/\Delta I_{2.3}|$. In this case, a first-order function, which can best separate the two groups of the discriminating parameters, is indicated by the following linear equation.

$Z = a_1 \times x_1 \times a_2 + x_2 + a_0$

Hereupon, a straight line 13, which indicates the boundary between the two groups of the discriminating parameters, is a graph in the case of $Z=0$, namely the following expression.

$0 = a_1 \times x_1 + a_2 \times x_2 + a_0$

Therefore, dividing the groups of discriminating parameters into two groups by the straight line 13 means dividing the groups of discriminating parameters into two groups in accordance with whether the value of Z according to the above-mentioned first-order function is plus or minus. In the case that the groups of discriminating parameters are divided into two groups by a curved line instead of the straight line, there may be used a high-order function for the discriminating parameters or independent variables, for example nth-order function (n=2, 3, 4 . . . ), as the discrimination function. Meanwhile, in the case that the number of the discriminating parameters is three, the discrimination function is indicated by the following expression.

$Z = a_1 \times x_1 + a_2 \times x_2 + a_3 \times x_3 + a_0$

In this case, the boundary is indicated by the graph of Z=0, namely the following expression.

$$0 = a_1 \times x_1 + a_2 \times x_2 + a_3 \times x_3 + a_0$$

This expression indicates a plane surface in a three dimensional space. In general, if the number of the discriminating parameters is P, the boundary, which is a (p−1) dimensional surface in a P dimensional space, is indicated by the following expression.

$$0 = a_1 \times x_1 + a_2 \times x_2 + a_3 \times x_3 + \ldots a_p \times x_p a_0$$

The samples were discriminated on the basis of the discriminating index value Z, which was calculated by substituting the value of the discriminating parameter obtained by the measurement into the discrimination function indicated by Expression 4 described above. In this case, based on the discriminating index value Z, the samples were discriminated in accordance with the following rule.

(1) In the case of Z<−8, it is judged that the sample is a control fluid.

(2) In the case of $-8 \leq Z \leq 8$, the judgement is not performed while it is decided that the sample is un-decidable.

(3) In the case of Z>8, it is judged that the sample is blood.

In the case of using the discrimination function indicated by Expression 4, which is defined in the concrete example, the rate of the erroneous judgement is 0.011%. Hereupon, the rate of the erroneous means a probability of the erroneous judgement when the kinds of the samples are discriminated in accordance with the sign while assuming that the discriminating index values Z of the two groups to be discriminated are distributed with the normal distribution. That is, in this concrete example, it is the average value of the probability of becoming Z<0 when the control fluids are measured and the probability of becoming $Z \geq 0$ when the blood samples are measured.

Table 1 described below shows results when the judgement is performed only on the basis of the sign of the discriminating index value without setting the un-decidable area, namely results in the case that it is judged to be a control fluid if $Z \geq 0$ while it is judged to be a blood sample if Z<0.

TABLE 1

Case without un-decidable area

| Sample | Results based on index value Z | |
|---|---|---|
| | Control fluids | Blood samples |
| Control fluids | 832 | 2 |
| Blood samples | 1 | 3348 |

On the other hand, when the un-decidable area is provided, no erroneous judgements occur at all. Table 2 described below shows results when the samples are not discriminated in the case of $-8 \leq Z \leq 8$ as described above. In this case, the probability of being judged to be not-decidable is 1.3% as to the control fluids, while it is 0.1% as to the blood samples. Hereupon, if it is judged to be un-decidable, into the system, the user must input such information that which sample the user has measured by the manual operation.

TABLE 2

Case with un-decidable area

| Sample | Results based on index value Z | | |
|---|---|---|---|
| | Control fluids | Un-decidable | Blood samples |
| Control fluids | 823 | 11 | 0 |
| Blood samples | 0 | 5 | 344 |

If kinds of samples are different from the above-mentioned ones, the current wave shapes are also different. Therefore, it is necessary to change the time points or numbers of calculating the discriminating parameters (I/ΔI) of the samples in accordance with the kinds of the samples.

As described above, in the biosensor system constructed according to the present invention, kinds of samples to be measured can be automatically recognized by the sensor system without charging any expenses to users, and then the results may be informed to the users. Further, in the biosensor system constructed as the above, when control fluids are measured, the users can recognize the states of the sensor system without troublesome works.

Industrial Applicability

As described above, the sample discriminating method according to the present invention is useful as a discriminating method in a sensor system for measuring the concentration of a target substance contained in a sample, and particularly is suitable for using in a biosensor for quantitating the concentration of glucose, cholesterol or the like contained in a body fluid such as blood by measuring the electric current.

What is claimed is:

1. A method of discriminating a sample for a sensor system which quantitates a concentration of a target substance contained in the sample by measuring electric current, said method comprising the steps of:

using a ratio of a measured current value to a time differential value of the current value as a discriminating parameter;

defining a discrimination function for discriminating kinds of a plurality of samples, said discrimination function using said discriminating parameter as an independent variable;

using a numeric value obtained by substituting the value of said discriminating parameter into said discrimination function, as a discriminating index; and discriminating the kind of any one of the plurality of samples based on said discriminating index, wherein said discrimination function is defined by means of an expression of a high degree for said discriminating parameter.

2. The method according to claim 1, wherein said discrimination function is defined by means of an expression using a plurality of said discriminating parameters.

3. The method according to claim 1, wherein the kinds of the samples to be discriminated are a body fluid and a control fluid.

4. The method according to claim 3, comprising the steps of:

judging whether said sensor system is operating properly or not based on a quantitated value of the concentration of the target substance; and indicating a result of the judging step.

5. The method according to claim 1, further comprising the step of:

indicating that the step of discriminating the kind of the sample has not been automatically performed when the discriminating index is within a predetermined range such that it is difficult to discriminate the kind of the sample.

6. The method according to claim 5, further comprising the step of:

designating that a manual operation is required when the discriminating index is within the predetermined range such that it is difficult to discriminate the kind of the sample.

* * * * *